United States Patent
Touraud et al.

(10) Patent No.: US 7,226,618 B1
(45) Date of Patent: Jun. 5, 2007

(54) COLLOIDAL SUSPENSION OF SUBMICRONIC PARTICLES AS VECTORS FOR ACTIVE PRINCIPLES AND METHOD FOR PREPARING SAME

(75) Inventors: Franck Touraud, Lyons (FR); Nathan Bryson, Millery (FR)

(73) Assignee: Flamel Technologies, Inc., Cedex (FR)

( * ) Notice: Subject to any disclaimer, the term of this patent is extended or adjusted under 35 U.S.C. 154(b) by 305 days.

(21) Appl. No.: 10/130,783

(22) PCT Filed: Oct. 11, 2000

(86) PCT No.: PCT/FR00/02831

§ 371 (c)(1),
(2), (4) Date: Aug. 5, 2002

(87) PCT Pub. No.: WO01/37809

PCT Pub. Date: May 31, 2001

(30) Foreign Application Priority Data

Nov. 23, 1999 (FR) .................................. 99 14751

(51) Int. Cl.
| A61K 9/14 | (2006.01) |
| A61K 9/16 | (2006.01) |
| A61K 9/20 | (2006.01) |
| A61K 9/22 | (2006.01) |
| A61K 9/48 | (2006.01) |

(52) U.S. Cl. ...................... 424/489; 424/489; 424/490; 424/491; 424/401; 424/451; 424/464

(58) Field of Classification Search ............. 514/772.4; 424/489
See application file for complete search history.

(56) References Cited

U.S. PATENT DOCUMENTS

| 4,351,337 | A | | 9/1982 | Sidman |
| 4,450,150 | A | | 5/1984 | Sidman |
| 5,286,495 | A | | 2/1994 | Batich et al. |
| 5,449,513 | A | | 9/1995 | Yokoyama et al. |
| 5,510,103 | A | | 4/1996 | Yokoyama et al. |
| 5,780,579 | A | | 7/1998 | Soula et al. |
| 5,904,936 | A | * | 5/1999 | Huille et al. ................. 424/489 |
| 6,180,141 | B1 | * | 1/2001 | Lemercier et al. .......... 424/489 |
| 6,630,171 | B1 | | 10/2003 | Huille et al. |
| 2001/0000510 | A1 | | 4/2001 | Sakurai et al. |

FOREIGN PATENT DOCUMENTS

| EP | 0 583 955 A2 | 2/1994 |
| EP | 0 734 720 A1 | 3/1996 |
| EP | 0 721 776 A1 | 7/1996 |
| FR | 2 746 035 | 9/1997 |
| WO | WO 88/01213 | 2/1988 |
| WO | WO 89/08449 | 9/1989 |
| WO | WO 91/06286 | 5/1991 |
| WO | WO 91/06287 | 5/1991 |
| WO | WO 9734584 | * 3/1996 |
| WO | WO 96/29991 | 10/1996 |
| WO | WO 97/02810 | 1/1997 |
| WO | WO 97/34584 | 9/1997 |
| WO | WO 02/28521 | 4/2002 |

OTHER PUBLICATIONS

Akiyoshi et al., *Stabilization of Insulin upon Supramolecular Complexation with Hydrophobized Polysaccharide Nanoparticle*, Chemistry Letters (1995), vol. N8, pp. 707-708.
N. Bryson et al., copending U.S. Appl. No. 10/398,134, filed Apr. 1, 2003 (filed as PCT/FR01/03083).
S. Candau, Chapter 3 Light Scattering, in *Surfactant Solutions*, vol. 22, Ed. R. Zana, M. Dekker, Inc. New York (1984), pp. 147-207.
W.D. Fuller, *A procedure for the facile synthesis of amino-acid N-carboxyanhydrides*, Biopolymers (1976) vol. 15, pp. 1869-1871.
Harada et al., *Formation of Polyion Complex Micelles in an Aqueous Milieu from a Pair of Oppositely-Charged Block Copolymers with Poly(Ethylene Glycol) Segments*, Macromolecules, (1995) vol. 28, pp. 5294-5299.
M.J. Humphrey, *Delivery System for Peptide Drugs*, eds. S Davis et al., Plenum Press, N.Y. (1986), pp. 139-151.
Kataoka, *Preparation of Novel Drug Carrier Based on the Self-Association of Block Copolymer*, Drug Delivery Systems, (1995) vol. 10, p. 363-70.
Tsutsumiuchi et al., *Synthesis of Polyoxazoline—(Glyco)peptide Block Copolymer Ring-Opening Polymerization of (Sugar-Substituted) α Amino Acid N-Carboxyanhydrides with Polyoxazoline Macroinitiators*, Macromolecules (1997) vol. 30, pp. 4013-4017.
Constancis et al. "Macromolecular Colloids of Diblock Poly(amino acids) That Bind Insulin" J. Colloid and Interface Sci. vol. 217, pp. 357-368 (1999).

* cited by examiner

*Primary Examiner*—Susan Tran
(74) *Attorney, Agent, or Firm*—Patton Boggs, LLP

(57) ABSTRACT

A suspension of vector particles (PV) based on polyamino acids and have a mean hydrodynamic diameter between 30 and 120 nm, and an insulin load factor of from 5 to 25% of associated insulin volume relative to the polyamino acid volume forming the vector particles. The polyamino acids are double-block polymers containing hydrophilic and hydrophobic monomers. The suspension may be prepared by copolymerizing N-carboxy anhydrides of hydrophobic monomers and precursors of hydrophilic monomers, in the presence of N-methyl pyrrolidone and methanol. The copolymer is optionally neutralized, subjected to dialysis, concentrated and water is eliminated to produce a solid powder, which can be suspended in a liquid to produce the colloidal suspension. Active principles such as insulin or vaccines are associated with the carrier particles to prepare special pharmaceutical products.

22 Claims, 2 Drawing Sheets

200 nm 50 nm

US 7,226,618 B1

COLLOIDAL SUSPENSION OF SUBMICRONIC PARTICLES AS VECTORS FOR ACTIVE PRINCIPLES AND METHOD FOR PREPARING SAME

This application is a U.S. National Stage of International application PCT/FR00/02831, filed Oct. 11, 2000, and published on May 31, 2001 in the French Language.

TECHNICAL FIELD

The field of the present invention is that of Vector Particles (PV), which are useful for the administration of active principles (PA). The latter are preferably medicaments or nutrients for administration to an animal or human organism by the oral, nasal, vaginal, ocular, subcutaneous, intravenous, intramuscular, intradermal, intraperitoneal, intracerebral or parenteral route, or the like. However, this may also involve cosmetic products or plant-production products, such as herbicides, pesticides, insecticides or fungicides, or the like. In terms of chemical nature, the PAs most particularly, but without limitation, involved in the invention are, for example, proteins, glycoproteins, peptides, polysaccharides, lipopolysaccharides, oligonucleotides, polynuclides and organic molecules.

The present invention relates, more precisely, to colloidal suspensions of Vector Particles, advantageously of the submicronic type, based on polyamino acids (PAA). The present invention relates to both uncoated particles as such, and vector systems for PAs, consisting of particles loaded with the PA(s) considered. The present invention also relates to pulverulent solids comprising these PVs. The invention also relates to methods for preparing said colloidal suspensions of particles, with or without PAs.

PRIOR ART

The encapsulation of PA into the PVs is intended in particular to modify their duration of action and/or to convey them to the site of treatment and/or to increase the bioavailability of said PAs. Numerous encapsulation techniques have already been proposed. Such techniques are intended, on the one hand, to allow the transport of the PA to its site of therapeutic action, while protecting it against attacks by the body (hydrolysis, enzymatic digestion and the like) and, on the other hand, to control the release of the PA at its site of action, in order to maintain the quantity available for the body at the desired level. The PAs involved in these vicissitudes of transport and of existence in the body are, for example, proteins, but may also be products which are completely different, organic molecules of synthetic or natural origin.

The review of M. J. HUMPHREY (Delivery system for peptide Drugs, published by S. DAVIS and L. ILLUM, Plenum Press, N.Y. 1986) reports the problem relating to the enhancement of the bioavailability of the PAs and the advantage of vector and controlled release systems.

Among all the materials which can be envisaged for forming PVs, polymers are increasingly used because of their intrinsic properties. As regards the specifications which it is desired to obtain for the PVs, they are particularly demanding and comprise, in particular, the following specifications:

1. The first specification desired for the PVs would be that the polymer constituting the PVs is biocompatible, capable of being eliminated (by excretion) and/or biodegradable and, even better, that it is metabolized into products which are not toxic for the body. In addition, it would be appropriate for the biodegradation in the body to be of a sufficiently short duration.
2. It would be advantageous for the PVs to be able to form a stable aqueous suspension without the aid of an organic solvent and/or a surfactant.
3. It would also be desirable for the PVs to have a sufficiently small size to be able to undergo, in suspension in a liquid, a sterilizing filtration by a filter whose pore diameter is less than or equal to 0.2 µm.
4. It is desirable for the PVs and the PV-PA systems to be obtained by a method which is nondenaturing for the PA.
5. The PVs advantageously ought to make it possible to control the rate of release of the PA.
6. Another important specification would be that the PV-PA systems can constitute excellent injectable medicaments. This enhanced capacity for administration by injection—e.g. intravenous or intramuscular injection—"injectability" is characterized by: (i) a reduced injected volume (for a given therapeutic dose) (ii) a low viscosity.

These two properties are satisfied when the therapeutic does of PA is associated with a minimal quantity of PA. In other words, the PVs should have a high PA load factor.

7. The cost specific to the PVs in an injectable preparation should be reduced and, here again, it is appropriate for the PVs to have a high PA load factor. In the final analysis, the small size and a high load factor are major specifications sought for the PVs.
8. It is also advantageous for the polymer constituting the PVs not to induce an immune response.

The earlier technical proposals, which are described below, have tried to satisfy all these specifications. By way of illustration, there may be mentioned the earlier proposals (a) to (h):

(a) U.S. Pat. No. 5,286,495 relates to a method of encapsulation by vaporization of proteins in aqueous phase, using materials having opposite charges, namely: alginate (negatively charged) and polylysine (positively charged). This method of manufacture makes it possible to produce particles having a size greater than 35 µm.

(b) Moreover, emulsion techniques are commonly used to prepare microparticles loaded with PA. For example, patent applications WO 91/06286, WO 91/06287 and WO 8908449 disclose such emulsion techniques in which organic solvents are used to solubilize polymers, for example of the polylactic type. However, it was found that the solvents may be denaturing, in particular for peptide or polypeptide PAs.

(c) Biocompatible PVs called proteinoids, which have been described since 1970 by X. FOX and K. DOSE in "Molecular Evolution and the Origin of Life", Ed. Marcel DEKKER Inc (1977), are also known. Thus, patent application WO 88/01213 proposes a system based on a mixture of synthetic polypeptides, whose solubility depends on the pH. To obtain the matrix microparticles according to this invention, they solubilize the mixture of polypeptides, and then with a change of pH, they cause the precipitation of proteinoid particles. When the precipitation is carried out in the presence of a PA, the latter is encapsulated into the particle.

(d) There may also be mentioned, as a reminder, patent U.S. Pat. No. 4,351,337 which belongs to a field which is different from that of the vectorization of PA which is specific to the invention. This patent discloses mass implants which are attached and located at quite precise sites in the body. These implants are hollow tubes or capsules of microscopic size (160 μm and having a length equal to 2 000 μm), consisting of copolymers of copoly(amino acids)—e.g. poly(glutamic acid-leucine) or poly(benzyl gluetamte-leucine)—which are obtained by copolymerization of monomers of N-carboxyanhydrides of amino acids (NCA). The inclusion of a PA occurs through a technique for evaporation of solvent for a mixture of polymer and of PA. U.S. Pat. No. 4,450,150 belongs to the same family as patent U.S. Pat. No. 4,351,337 studied above and essentially has the same object. The constituent PAAs are poly (glutamic acid-ethyl glutamate).

(e) Patent application PCT/FR WO 97/02810 discloses a composition for the controlled release of active principles, comprising a plurality of lamellar particles of a biodegradable polymer, which is at least partially crystalline (lactic acid polymer) and of a PA absorbed onto said particles. In this case, the release of the active principle occurs by desorption.

(f) The publication "CHEMISTRY LETTERS 1995, 707, AKIYOSHI ET AL" relates to the stabilization of insulin by supramolecular complexing with polysaccharides hydrophobized by grafting of cholesterol.

(g) The article which appeared in "MACROMOLECULES 1997, 30, 4013–4017" describes copolymers composed of a polypeptide block based on L-phenylalanine, (-benzyl-L-glutamate or O-(tetra-O-acetl-D-glucopyranosyl)-L-serine, and a synthetic block, such as poly(2-methyl-2-oxazoline) or poly(2-phenyl-2-oxazoline). Polymers aggregate in aqueous medium to form particles of 400 nm, which are capable of combining with an enzyme, lipase. The term combined means here that the protein adsorbs onto the particle by a physical phenomenon (no covalent bonding).

(h) Patent application FR 2 746 035 describes in particular, page 28, lines 3 to 16, a colloidal suspension of composite gel microparticles, obtained from a polyamino acid of the polypolyleucine/sodium glutamate type, fractionated coconut oil (miglyol®) and deionized water or buffered saline solution (phosphate buffer pH 7.4 at 25° C.). The mean reference diameter D[4,3] of these composite gel microparticles is 2 800 nm. It is evident from all the examples of FR 2 746 035, that the smallest mean reference diameter D[4,3] is equal to 1 900 nm.

Moreover, these composite gel microparticles cannot combine with insulin in the nondissolved state in colloidal suspension, according to a factor Ta≧7%. Under these conditions, it is obvious that the composite gel microparticles do not meet the specifications, and in particular not the specifications relating to injectability and to the capacity for combination and for release in relation to insulin.

In addition, the method according to FR 2 746 035 does not involve a nonaromatic polar solvent and the formation of microparticles does not occur spontaneously in aqueous medium, but involves the use of vigorous homogenization with the aid of a rotor/stator type device.

(i) The subject of PCT application WO 96/29991 is polyamino acid particles useful for the vectorization of PA. These particles have a size of between 10 and 500 nm, preferably between 30 and 400 nm. In the examples of this PCT application, the size of the particles is measured by the radius of gyration. The radius of gyration of the particles obtained in these examples varies from 55 to 280 nm. Other techniques exist for measuring the size of colloidal particles. The determination of the mean hydrodynamic diameter (Dh) of the particles by quasi-elastic light scattering (QELS) is an example of a convenient method of measurement. In the whole of the present disclosure, an Md procedure for measuring Dh is taken as reference. Md is described later. Thus, the Dh of the particles according to the examples of the PCT WO 96/29991 extends from 150 nm to 750 nm. It is to be noted that the PVs in question here consist of a hydrophobic core surrounded by hydrophilic hair. The hydrodynamic diameter of these objects is less than double their radius of gyration, as will be explained, for example, in the books "Dynamic Light Scattering", B. J. Berue and R. Pecaran (Wiley, 1976) and "Physicochemical Hydrodynamics", R. F. Probstein (Wiley 1994). The load factor Ta for the particles is conveniently expressed by the ratio of the mass of insulin to the mass of dry PV. According to the examples of WO 96/29991, with a PA consisting of insulin, is at best 0.065 mg/mg, that is 6.5% by dry weight of insulin relative to the mass of PAA. Ta is measured according to a procedure Ma described later. The particles according to WO 96/29991 form spontaneously by bringing PAA into contact with an aqueous solution. The PAAs comprise neutral and hydrophobic amino acid monomers AAO and ionizable and hydrophilic monomers AAI. These PAAs are prepared by copolymerization of NCA of AAI precursors (e.g.: Glu-OMe) and of NCA of AAO (e.g. Leu) in solution in a dioxane/toluene mixture. The copoly(Glu-OMe) (Leu) obtained in solution is recovered by precipitation in water, filtration and drying. This copolymer is then subjected to acid hydrolysis by incorporating it into TriFluoroAcetic acid (TFA), in which is dissolves. A copolymer (Glu-O-Na) (Leu) is recovered after neutralizing, dialysis, filtration and freeze-drying. This coPAA is dispersed in an aqueous solution of NaCl and a suspension of nanoparticles spontaneously forms. As indicated above, the latter have a Dh size greater than 150 nm and an insulin load factor Ta of 6.50%.

It is therefore evident from the above that the earlier technical proposals described above, and in particular proposal (i), incompletely satisfy the new specifications indicated above, and in particular a capacity for sterilizing by filtration, a high rate of degradation, adaptability to constraints for administering medicaments by injection, low cost and high PA load factor.

As regards the sterilizing filtration capacity, it is important that the PV particles are sufficiently small to pass, in suspension in a liquid, across filters whose cut-off is less than or equal to 0.2 μm, without clogging. Such ease and efficiency of filtration sterilization are particularly appreciated for injectable medicaments.

As regards the capacity for injection of the PVs, it is appropriate, for a given dose of PA, to be able to inject small volumes of liquid suspension, and that this suspension is not very viscous. This involves being able to reduce the quantities of excipient (PV) compared with the targeted therapeutic dose of PA and to provide PVs having a size which is as small as possible, while increasing the loading capacity of PA.

As regards the specification relating to biodegradability of the PVs, the smaller the size of the PVs, the better it is and it allows their rapid elimination.

In addition, it is appreciable to be able to reduce the quantities of excipient (PV) for economic reasons and so as to enhance the tolerance of the injectable medicament.

BRIEF DISCLOSURE OF THE INVENTION

Under these circumstances, an essential objective is to be able to provide novel PVs which spontaneously form, and without the aid of surfactants or of organic solvents, stable aqueous suspensions of PV.

Another essential objective of the present invention is to provide novel PSv in stable aqueous colloidal suspension or in pulverulent form and based on poly(amino acids) (PAA), these novel PVs having to satisfy as much as possible specifications 1 to 8 of the abovementioned specifications.

Another essential objective of the invention is to improve the particles disclosed in PCT application WO 96/29991.

Another essential objective of the invention is to provide a novel suspension of PV whose characteristics are perfectly controlled, in particular in terms of PA load factor and in terms of control of kinetics of release of PA.

Another essential objective of the invention is to provide injectable medicinal suspensions. The specifications, which are required for such suspensions, are a low volume for injection and a low viscosity. It is important for the mass of colloidal particles per injection dose to be as low as possible, without limiting the quantity of active principle PA transported by these particles, so as not to damage the therapeutic efficacy.

Another essential objective of the invention is to provide an aqueous colloidal suspension or a pulverulent solid comprising particles for carrying active principles satisfying the specifications targeted above and which constitutes an appropriate and suitable galenic form for administration, for example oral administration, to humans or animals.

Another essential objective of the invention is to provide a colloidal suspension comprising particles for carrying active principles which can be filtered on 0.2 μm filters for sterilization purposes.

Another essential objective of the invention is to propose a method for preparing PAA particles (dry or in suspension in a liquid) which are useful in particular as vectors for active principles, it being necessary for said method to be simpler to use, nondenaturing for the active principles and, in addition, to always allow fine control of the mean particle size of the particles obtained.

Another essential objective of the invention is the use of the abovementioned particles in aqueous suspension or in solid form for the preparation:

- of medicaments (e.g. vaccines), in particular for administration, in particular oral, nasal, vaginal, ocular, subcutaneous, intravenous, intramuscular, intradermal, intraperitoneal, intracerebral or parenteral administration, it being possible for the active principles of these medicaments to be, in particular, proteins, glycoproteins, peptides, polysaccharides, lipopolysaccharides, oligo-nucleotides and polynucleotides,
- and/or of nutrients,
- and/or of cosmetic or plant-protection products.
- and/or of organic medicinal molecules.

Another essential objective of the present invention is to provide submicronic PV suspensions based on PAA and capable of serving as vector for a PA, in particular one which is medicinal, for administration of said PA to a human or animal organism, or alternatively for a nutritional, plant-protection or cosmetic PA.

Another objective of the present invention is to provide a medicament, such as the system for prolonged release of active principles, which is easy and economical to produce and which is, in addition, biocompatible and capable of providing a very high level of bioavailability of the PA.

Another essential objective of the invention is to provide a system for carrying a vaccine, which is intrinsically nonimmunogenic and in combination with one or more antigens.

The objectives relating to the products (inter alia) are achieved by the present invention which relates, first of all, to a stable colloidal suspension of submicronic structured particles which can be used, in particular for carrying active principle(s) PA(s), these particles being individualized (discrete) supramolecular arrangements:

○ based on linear, amphiphilic polyamino acids (PAA), with peptide linkages and comprising at least two different types of recurring amino acids: hydrophilic AAI and hydrophobic neutral AAO, the amino acids of each type being mutually identical or different, ○ and capable of combining in colloidal suspension, in the nondissolved state, at least one PA and of releasing it, in particular in vivo, in a prolonged and/or delayed manner, characterized:

● in that the AAI(s) of the polymer chains is(are) chosen from amino acids with an ionizable side chain, the natural amino acids Glue and Asp in carboxylic form and/or in the form of salts being particularly preferred, ● in that the AAO(s) of the polymer chains is(are) chosen from the group comprising natural neutral amino acids, preferably those belonging to the subgroup comprising: Leu, Ile, Val, Ala, Gly, Phe;

● in that the particles are stable in aqueous phase at pH between 4 and 13 in the absence of surfactant(s), ● by a load factor Ta for the vector particles with insulin, expressed as % of combined insulin mass relative to the mass and measured according to a procedure Ma, Ta being such that: $7 \leq Ta$ preferably, $8 \leq Ta \leq 50$ and, still more preferably, $10 \leq Ta \leq 30$ ● and by a mean hydrodynamic diameter Dh expressed in nanometers (nm) and measured according to a procedure Md, Dh being such that: $10\ nm \leq Dh \leq 150\ nm$ preferably, $20\ nm \leq Dh \leq 100\ nm$.

DETAILED DESCRIPTION OF THE INVENTION

The procedures Md and Ma for the Dh and Ta measurements are detailed below.

Procedure Md:

The pulverulent PAA powder is suspended in a 0.15 M aqueous sodium chloride solution at pH 7.4, 25° C. and at a polymer concentration of between 0.01 and 0.5 g/l and, preferably, equal to 0.1 g/l. This suspension is stirred for 4 hours, and then introduced into the scattering cell of a light scattering apparatus, of the Brookhaven type, functioning with a laser beam having a wavelength of 488 nm and vertically polarized. The hydrodynamic diameter is calculated from the electric field autocorrelation function by the cumulant method, as described in the manual "Surfactant Science Series" volume 22, Surfactant Solutions, Ed. R. Zana, chap. 3, M. Dekker, 1984.

Procedure Ma:
(a) Preparation of an aqueous insulin solution: freeze-dried human recombinant insulin (Sigma No. 10259) is poured into a 0.1 N HCl solution over 5 min at 25° C. This solution is then poured into a phosphate buffer solution which is finally neutralized by adding 0.1 N NaOH. The solution is then allowed to stand for 30 min at room temperature, and then filtered on 0.8–0.2 µ acrodisc membrane. The mass of insulin is calculated according to the desired volume of solution, in order to obtain a concentration of 60 IU/ml.
(b) Dispersion of the vector particles in PAA to be combined in the insulin solution: the freeze-dried PVs are added to the insulin solution, in an amount of 10 mg PV/ml of solution. This mixture is stirred on a vortex two or three times, and then placed in a rocking shaker at room temperature for 18 hours. The colloidal suspension is then stored at 4° C.

(c) Separation of free insulin from combined insulin and assay of free insulin: the solution containing the insulin and the PVs is centrifuged for 1 hour at 60 000 g at 20° C. The supernatant is placed in tubes provided with an ultrafiltration membrane (cut-off 100 000 Da) and centrifuged at 3 000 g, 2 hours at 20° C. The insulin in the filtrate is assayed by HPLC.

One of the inventive bases of these novel vector particles PV, in stable aqueous colloidal suspension or in the form of pulverulent solid, is due to the innovative selection of a group of polymers and of an innovative methodology which make it possible to obtain particles of submicronic size, which form a stable aqueous colloidal suspension in the absence of surfactants or solvents.

Another inventive basis of these novel vector particles PV, in stable aqueous colloidal suspension or in the pulverulent solid state, is due to the innovative selection of a group of particular submicronic structured particles by their load factor Ta≧7% and their size Da≦150 nm. This selection is the result of major and long research studies on the method for producing the particles. Indeed, the reduction in size and the increase in the loading capacity of the particles of polyamino acids was a priori not obvious. Thus, using the method for producing nanoparticles of polyamino acid taught in PCT application WO 96/29991, persons skilled in the art were not able to obtain, "to measure", particles which correspond to the new specifications, as defined above.

Finally, it is by modifying the compositions of the polymers and the operating conditions that the inventors were able to isolate these structured particles of very small size which are based on PAA and which have, quite surprisingly and unexpectedly, a load capacity Ta for insulin which may be up to three times higher than that characteristic of the particles according to WO 96/29991.

Advantageously, the suspension according to the invention is characterized in that the submicronic particles do not acquire their cohesion from the presence of the following three compounds:

I) oil

II) aqueous phase

III) and at least one synthetic non-crosslinked linear copolyamino acid comprising at least two different types of amino acid comonomer: hydrophilic AAI and hydrophobic AAO, unlike the suspension of micrparticles according to patent application FR 2 746 035.

The structure of the PAA polymers and the nature of the amino acids are chosen such that:

- the polymer chains are spontaneously structured in the form of small-sized particles (PV),
- the particles form a stable colloidal suspension in water and in physiological medium,
- the PVs combine with proteins or other PAs in aqueous medium, by a spontaneous mechanism which is non-denaturing for the protein,
- the PVs release the PAs in physiological medium and, more precisely, in vivo; the kinetics of release depend on the nature of the PAA polymer which is the precursor of the PVs.

Thus, by modifying the particular structure of the PAA, it is possible to control the phenomena for combining and releasing the PA from the kinetic and quantitative point of view.

It is to the applicant's credit to have chosen, as constituent material of the PVs, a particular composition of polyamino acids which are amphiphilic and which therefore possess properties of the PVs in PAA, namely:

- possibility of spontaneously forming colloidal suspensions of PV which are compatible with the pH of the physiological media encountered in the therapeutic applications targeted,
- spontaneous combination of the PAs with PVs in the absence of another agent apart from water which serves as solvent for them and which, in the case of proteins, is not denaturing,
- possibility of releasing the PA from the PA-PV combination complex, under physiological conditions, with pharmacokinetic and pharmacodynamic profiles, which make it possible to envisage advantageous uses in the therapeutic field (PA vectorization), and which, moreover, have novel properties which are:
- filterability with a cut-off of less than or equal to 0.2 μm for sterilization purposes,
- improved biodegradability,
- optimized injection capacity.

It was possible to obtain these new properties by virtue of the primary technical functions of the PVs which are the small nanometric size and the high load factor.

To define these PAAs a little further, it is possible to indicate that they can be of the alternating sequential, ordered (block) type or of the random sequential, disordered type.

Thus, according to a first embodiment of the PVs according to the invention, the constituent PAAs are of the "block" type and are characterized by an AAO/(AAI+AAO) molar ratio such that:

- 10%≦AAO/(AAO+AAI)≦70%,
- preferably, 20% AAO/(AAI+AAO)≦60%,
- and still more preferably, 35% ≦ AAO/(AAI+AAO) ≦50%.

Advantageously, the absolute length of each AAO block, expressed as number of AAO is such that:

- preferably, AAO>10,
- and, still more preferably, 20≦AAO≦100.

According to a second embodiment of the PVs according to the invention, the constituent PAAs are of the "random" type, that is to say are prepared by simultaneous copolymerization of AAI and AAO monomers, and the AAO/(AAO+AAI) molar ratio is such that:

- AAO/(AAO+AAI)>10%,
- and, preferably, AAO/(AAO+AAI)≧20%,
- and, still more preferably, 30%≦AAO/(AAI+AAO) ≦70%.

Advantageously, the molar mass Mw of these random PAAs is such that:

- Mw ≧ 2 000 g/mol,
- preferably, Mw ≧ 5 500 g/mol,
- and still more preferably, 5 500 g/mol ≦ Mw ≦ 200 000 g/mol.

According to a preferred characteristic of the invention, the constituent block or random PAAs of the particles have degrees of polymerization DP of between 30 and 600, preferably between 50 and 200, and still more preferably between 60 and 150.

Advantageously, the constituent PAAs of the PV particles are "diblock" PAAs.

The present invention relates, not only to suspensions of uncoated particles, as defined above, but also to particles comprising at least one active principle PA. Preferably, the suspension according to the invention is aqueous and stable. These particles, loaded or not with PA, are advantageously in dispersed form in a liquid (suspension), preferably an aqueous liquid, but may also be in a pulverulent solid state, obtained from the suspension of PV as defined above.

Accordingly, the invention relates, apart from to a colloidal suspension (preferably aqueous suspension) of PV, to a pulverulent solid comprising PVs and obtained from the suspension according to the invention.

Another essential subject of the invention relates to the preparation of the selected particles (as described above), both in the form of a colloidal suspension and in the form of a pulverulent solid. The method of preparation considered essentially consists in synthesizing precursor PAAs and in converting them to structured particles.

More precisely, this includes, first of all, a method for preparing submicronic structured particles capable of being used, in particular for carrying active principle(s), these particles being discrete supramolecular arrangements:
- based on linear amphiphilic polyamino acids (PAA), with linkages (-AAI hydrophilic and AAO hydrophobic, the amino acids of each type being mutually identical or different;
- having a mean diameter Dh, expressed in nm and measured according to a procedure Md, such that: 10 ≦ Dh ≦ 150 preferably, 20 ≦ Dh ≦ 100;
- on the one hand capable of forming a stable colloidal suspension by simple mixing in an aqueous medium, without it being necessary to add a solvent or surfactants thereto;
- and on the other hand, capable of combining in a liquid medium, with at least one PA and, in particular, with insulin according to a load factor Ta, expressed as %, and measured according to a procedure Ma such that: 7 ≦ Ta, preferably 8 ≦ Ta ≦ 25, and, on the other hand, of releasing it, in particular in vivo, in a prolonged and controlled manner.

This method is characterized in that:
1. a copolymerization of monomers N-Carboxy-Anhydrides of amino acids (NCA) of at least two different types, on the one hand, NCAs-pAAI ("pAAI" designating a precursor of AAI) and, on the other hand, NCAs-AAO, is carried out in the presence:
   ○ of at least one nonarmoatic polar solvent, preferably chosen from the group comprising: N-MethylPyrrolidone (NMP), DiMethylFormamide (DMF), Dimethyl Sulfoxide (DMSO), DiMethylAcetamide (DMAc), pyrrolidone, NMP being most particularly preferred,
   ○ and, optionally of at least one protic cosolvent preferably chosen from the group comprising pyrrolidone, water, alcohols; methanol being particularly preferred;
2. the recurring pAAI motifs of the precursor PAA copolymer of the particles are converted to recurring AAI motifs, using hydrolysis, preferably acid hydrolysis, for which an aqueous acid phase is added to the organic medium described above;
3. optionally, the reaction medium is neutralized;
4. optionally, the reaction medium is purified by dialysis in order to obtain an aqueous suspension of structured particles;
5. optionally, this suspension is concentrated;
6. optionally, the liquid medium is removed in order to collect the pulverulent solid comprising the particles.

The first step of the method is based on known techniques of polymerization of anhydrides of N-carboxy-(-amino acids (NCA), described, for example, in the article "Biopolymers, 15, 1869 (1976)" and in the book by H. R. KRICHELDORF "(-Aminoacid-N-carboxy Anhydride and Related Heterocycles" Springer Verlage (1987). The use of judiciously chosen polar nonaromatic aprotic copolymerization solvents, while avoiding any precipitation and the use of acid hydrolysis in the presence of water and of nonaromatic polar organic solvent, constitute novel and inventive modalities which lead to structured, discrete and submicronic particles with a high PA load capacity, and which form a stable colloidal suspension in aqueous medium. These particles are not at all comparable to a macroscopic agglomerated precipitate of the type mentioned above in relation to the earlier proposal (d).

According to one variant, at the end of step 1, the copolymer poly(AOO) (pAAI) obtained is precipitated—preferably in water—and this precipitate is recovered. This variant corresponds to a batch mode for preparing particles, in which the copolymer poly(AAO) (pAAI) is isolated in the form of a precipitate forming a stable intermediate product. This precipitate may be, for example, filtered, washed and dried.

Still more preferably, the NCA-pAAI are NCAs of O-alkylated glutamic or aspartic acid, for example NCA-Glu-O-Me, NCA-Glu-O-Et or NCA-Glu-O-Bz (Me=methyl–Et=ethyl–Bz=benzyl).

In a known manner, the copolymerization takes place at a temperature between 20 and 120° C., at atmospheric pressure and in the presence of an amine-containing initiator, e.g.: $NH_3$. Other experimental parameters, such as the concentration of NCA and/or polymer in the nonaromatic polar solvent (preferably NMP), and/or the concentration or the nature of the protic cosolvent, during the synthesis, will be adjusted according to the desired effects known to persons killed in the art. The acid hydrolysis (step 2) is carried out using water and at least one inorganic acid such as phosphoric or hydrochloric aid—the latter being preferred—and/or an organic acid, such as TriFluoroAcetic acid (TFA), acetic acid, dichloroacetic acid or organosulfonic acids.

The water/acid ratios—expressed in parts by weight—in an acidic aqueous phase for hydrolysis are advantageously:
- from 60/1 to 2/1,
- preferably 40/1 to 2/1,
- and, still more preferably, 20/1 to 2/1.

The acid aqueous phase for hydrolysis/NMP ratios—expressed in parts by weight—are advantageously:
- from 5/100 to 200/100
- preferably 10/100 to 100/100
- and still more preferably from 20/100 to 80/100.

Other parameters, such as the polymer concentration, the temperature of the reaction mixture, the mode of adding the acidic aqueous phase for hydrolysis, the use of reduced pressure, the duration of the reaction, and the like, are adjusted according to the desired effects and are well known to persons skilled in the art.

The neutralization (step 3) is carried out in practice, for example, using sodium hydroxide.

The salt form after neutralization as well as the solvent are then removed by any appropriate physical separation treatment, for example by diafiltration (dialysis) (step 4), filtration, pH modification, chromatography and the like.

This gives an aqueous suspension of structured particles which may be concentrated, for example, by distillation or any other suitable physical means: ultrafiltration, centrifugation.

To separate, in step 6, the particles from their liquid suspension medium, the aqueous phase is optionally removed, for example, by drying (e.g. in an oven) by freeze-drying or any other suitable physical means: ultrafiltration, centrifugation. A white pulverulent solid is recovered at the end of this step 6.

According to one variant, the concentration step may be carried out by a chemical treatment, such as a reduction in the pH, which converts to an acid the hydrophilic part of the glutamate monomers, making them insoluble in water. These acidic PAA intermediates may be filtered, washed and dried. Said acidic intermediates may be neutralized with a chemical base in a subsequent step in order to obtain a suspension of particles.

It should be noted that the use of steps 1, 2, 3, 4 and optionally 5 of the above method corresponding to a preparation of a colloidal suspension of submicronic particles and to a high load factor with the PAs.

During this preparation of colloidal suspension, the amphiphilic PAAs poly(AAO) (AAI) of step 2 are placed in an aqueous medium in which at least part of the AAIs is soluble and at least part of the AAOs is insoluble. The PAAs exist in the form of nanoparticles in this aqueous medium.

An alternative for preparing the PV suspension according to the invention consists in bringing the pulverulent solid, as described above and as product and by its method of production, into contact with a nonsolvent aqueous medium for the AAOs.

To carry out the combination of one or more PAs with the particles, it is possible to use several methods in accordance with the invention. Nonlimiting examples of these methods are listed below.

According to a first method, the combination of PA with the particles is carried out by bringing a liquid phase (aqueous or otherwise) containing the PA into contact with the colloidal suspension of particles.

According to a second method, the combination of the PA with the particles is carried out by bringing a PA in the solid state into contact with the colloidal suspension of particles. The solid PA may be, for example, in freeze-dried, precipitate or powdered form or the like.

According to a third method, the pulverulent solid (PAA), as described above as product and by its production characteristics, is brought into contact with a liquid phase (aqueous or otherwise) containing the PA.

According to a fourth method, the pulverulent solid, as described above as product and by its production characteristics, is brought into contact with the PA in solid form. This mixture of solids is then dispersed in a liquid phase, preferably an aqueous solution.

In all these methods, the PA used may be in pure or preformulated form.

Given the nanometric size of the particles, the suspension may be filtered on sterilizing filters, which makes it possible to obtain, easily and at a lower cost, sterile injectable medicinal liquids. The fact that it is possible, by virtue of the invention, to control the size of the particles and reach Dh values of between 25 and 100 nm, is a major advantage.

The present invention also relates to novel intermediate products of the method described above, characterized in that they consist of PAA copolymers which are precursors of particles.

INDUSTRIAL APPLICATION

According to another of its aspects, the invention relates to a suspension and/or a pulverulent solid, as defined above and/or as obtained by the method presented above, this suspension and this solid comprising at least one active principle preferably chosen from:
- vaccines,
- proteins and/or peptides, among which those most preferably selected are: hemoglobins, cytochrome, albumins, interferons, antigens, antibodies, erythropoietin, insulin, growth hormones, factors VIII and IX, interleukins or mixtures thereof, hematopoiesis-stimulating factors,
- polysaccharides, heparin being more particularly selected,
- nucleic acids and, preferably, RNA and/or DNA oligonucleotides,
- non-petido-protein molecules belonging to various anticancer chemotherapy classes and, in particular, anthracyclines and taxoids,
- and mixtures thereof.

The invention also relates to a suspension and/or the pulverulent solid loaded with nutritional, plant-protection or cosmetic PA.

Finally, the invention relates to a pharmaceutical, nutritional, plant-protection or cosmetic proprietary product, characterized in that it comprises a suspension and/or the pulverulent solid loaded with PA and as defined above.

According to another of its subjects, the invention also relates to the use of these PVs (in suspension or in solid form) loaded with PA, for the manufacture of medicaments such as systems with controlled release of PA.

In the case of medicaments, they may be, for example, those which can be administered, preferably by the oral, nasal, vaginal, ocular, subcutaneous, intravenous, intramuscular, intradermal, intraperitoneal, intracerebral or parenteral route.

The cosmetic applications which may be envisaged are, for example, compositions comprising a PA combined with the PVs according to the invention and which can be applied by the transdermal route.

The relevant plant-protection products may be, for example, herbicides, pesticides, insecticides, fungicides and the like.

The following examples will make it possible to better understand the invention in its various product/method/application aspects. These examples illustrate the preparation of particles of polyamino acids loaded or otherwise with active principles, and they likewise present the structural characteristics and the properties of these particles.

EXAMPLES

Example 1

Figure 1:
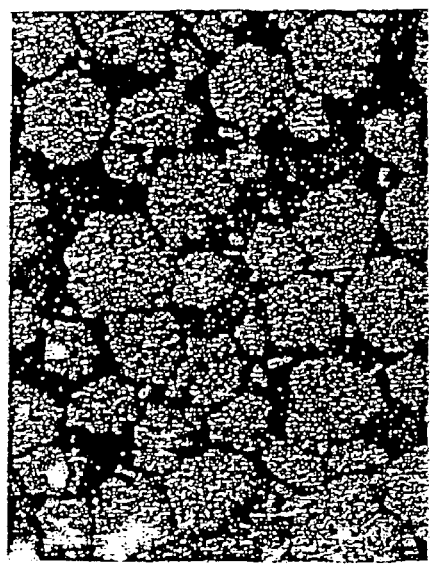
FIG. 1: Nanoparticles corresponding to a block copolymer Ia: leucine 50/glutamate 50 obtained according to the teaching of patent WO 96/29991.

Production, in aqueous stable colloidal suspension and in pulverulent solid form, of vector particles, from a block polyamino acid, poly(Leu/Glu) 40/80 diblock 112.4 g of NCA-GluOMe (0.60 mol) and 449 go of N-methyl-2-pyrrolidinone (NMP) are introduced, with stirring, into a 1 liter reactor thermostated at 20° C. After dissolution, 21.38 g of a 0.34 M solution of ammonia in 1,4-dioxane (1.25 mol %/NCA) are added. The polymerization is monitored by measuring the carbon dioxide emitted into a gas bell jar and verified by disappearance of vibration bands characteristic of the NCAs at 1860 and 1790 $cm^{-1}$. After 30 min, a solution of 47.17 g of NCA Leucine (0.30 mol) in 631 g of NMP is introduced. After 10 min of reaction, the temperature is increased to 60° C. The polymerization is monitored as above and is complete after 2 hours. The temperature of the reaction mixture obtained is increased to 80° C. 31.5 g of aqueous concentrated hydrochloric acid (35%, 12 M) are added, with mechanical stirring over 30 min, to 350 g of the reaction mixture obtained at the end of step 1. The reactor is then placed under reduced pressure regulated at 600 mBar for 6 hours. A mixture of 31.5 g of 35% hydrochloric acid and of 126 g of water is then added over 60 min, followed by a second phase of vacuum at 250 mBar for 18 hours. In this example, the overall water/pure hydrochloric acid ratio is 7.6/1 by mass and the acidic aqueous phase/NMP ratio is 60/100 by mass.

The reaction mixture is then cooled to 50° C. and then neutralized with aqueous sodium hydroxide (35% by mass). The NMP and the sodium chloride formed during the neutralization are removed by diafiltration against 20 volumes of Milli Q water, on a membrane with an MWCO of 1 000 Daltons (Pellicon II system, Millipore). A stable aqueous colloidal suspension of vector nanoparticles is thus obtained. The suspension of nanoparticles is finally freeze-dried.

The contents of leucine motifs are determined by proton nuclear magnetic resonance (signals at 2.10, 2.22 and 2.58 ppm for 4H of Glu and at 0.85 ppm for 6H of Leu). The mean hydrodynamic diameter (Dh) is 70 nm (according to Md).

Example 2

Combination of insulin with the nanoparticles of poly(Leu/Glu) 40/80

The procedure Ma is used. The concentration of free insulin, assayed by HPLC chromatography is equal to 0.59 mg/ml and the combined insulin concentration equal to 1.51 mg/ml is deduced therefrom. The load capacity for a colloidal solution of 10 mg/ml reaches 1.51 mg/ml of insulin. Thus, the ratio of the mass of combined insulin to the bLE (Ta) mass is 15.1%.

Example 3

Production, in stable colloidal aqueous suspension and in pulverulent solid form, of vector particles from a block PAA poly(Leu/glu) 25/70 biblock 146.4 g of NCA GluOMe are dissolved in 586 g of NMP of which 18.43 g of a 0.48 M solution of ammonia in methanol are added. When the polymerization of the NCA GluOMe is complete, a solution of 43.9 g of NCA Leu in 708 g of NMP is introduced and the polymerization of the NCAs Leu is continued until disappearance of the monomers is obtained. The medium is then heated to 80° C. and 129.4 g of 35% HCl are added dropwise thereto over 30 min to 1 hour. A 600 mBar vacuum is applied for 6 hours, and then an additional 129.4 g of 35% HCl are added as a mixture with 517.5 g of water. A 250 mBar vacuum is then applied for 18 hours. After this step, the temperature is reduced to 50° C., 1 liter of water is introduced, followed by 280 ml of 35% NaOH in order to bring the pH to 7.4. The suspension is then filtered (5 μm), dialyzed (cut-off 1 000 Da) in water, in order to remove the solvent and the salts, and finally filtered (0.22 μm). This suspension may be directly used or may be subjected to subsequent treatments, such as distillation of the water (step 5) or freeze-drying (step 6).

The mean hydrodynamic diameter Dh (according to Md) is 14.8%. The insulin load factor Ta, determined according to the procedure Ma, is 35 nm.

Example 4

Production, in stable aqueous colloidal suspension, of vector nanoparticles, from a block polyamino acid, poly(Leu/Glu) 50/70 diblock and characteristics of the nanoparticles.

38.9 g of NCA-GluOMe (0.208 mol) and 156 g of N-methyl-2-pyrrolidinone (NMP) are introduced, with stirring, into a 0.5 liter reactor thermostated at 30° C. After dissolution, 5.79 g of a 0.407 M solution of ammonia in methanol (1.25 mol %/NCA) are added. The polymerization is monitored by measuring the carbon dioxide emitted into a gas bell jar and verified by disappearance of vibration bands characteristic of the NCAs at 1860 and 1790 $cm^{-1}$. After 30 min, a solution of 23.3 g of NCA Leucine (0.148 mol) in 263 g of NMP is introduced. After 10 min of reaction, the temperature is increased to 60° C. The polymerization is monitored as above and is complete after 1–2 hours. The temperature of the reaction mixture obtained previously is increased to 80° C. 41.9 g of aqueous hydrochloric acid (35% of the mass) are added, with mechanical stirring over 30 min, to the reaction mixture. The reactor is then placed under reduced pressure regulated at 600 mBar for 6 hours. A mixture of 41.9 g of 35% hydrochloric acid and of 167.5 g of water is then added over 60 min, followed by a second phase of vacuum at 250 mBar for 18 hours. The reaction mixture is then cooled to 50° C. and then neutralized with aqueous sodium hydroxide (35% by mass). The NMP and the sodium chloride formed during the neutralization are removed by diafiltration against 20 volumes of Milli Q water, on a membrane with an MWCO of 1 000 Daltons (Pellicon II system, Millipore). A stable aqueous colloidal suspension of vector nanoparticles is thus obtained. The suspension of nanoparticles is finally freeze-dried.

The mean hydrodynamic diameter Dh is measured according to Md on aqueous suspensions of the freeze-dried products. The insulin load factor Ta is determined according to the procedure Ma.

Example 5

Production, in stable aqueous colloidal suspension of vector nanoparticles, from a block polyamino acid, poly(Leu/Glu) 25/35 diblock and characteristics of the nanoparticles 38.9 g of NCA-GluOMe (0.208 mol) and 156 g of N-methyl-2-pyrrolidinone (NMP) are introduced, with stirring, into a 0.5 liter reactor thermostate at 30° C. After dissolution, 5.78 g of a 0.452 M solution of ammonia in methanol (1.25 mol %/NCA) are added. The polymerization is monitored by measuring the carbon dioxide emitted into a gas bell jar and verified by disappearance of vibration bands characteristic of the NCAs at 1860 and 1790 $cm^{-1}$. After 30 min, a solution of 23.3 g of NCA Leucine (0.149 mol) in 5 219 g of NMP is introduced. After 10 min of reaction, the temperature is increased to 60° C. The polymerization is monitored as above and is complete after 1–2 hours. The temperature of the reaction mixture obtained previously is increased to 80° C. 42.0 g of aqueous hydrochloric acid (35% of the mass) are added, with mechanical stirring over 30 min, to the reaction mixture. The reactor is then placed under reduced pressure regulated at 600 mBar for 6 hours. A mixture of 42.0 g of 35% hydrochloric acid and of 167.9 g of water is then added over 60 min, followed by a second phase of vacuum at 250 mBar for 18 hours. The reaction mixture is then cooled to 50° C. and then neutralized with aqueous sodium hydroxide (35% by mass). The NMP and the sodium chloride formed during the neutralization are removed by diafiltration against 20 volumes of Milli Q water, on a membrane with an MWCO of 1 000 Daltons (Pellicon II system, Millipore). A stable aqueous colloidal suspension of vector nanoparticles is thus obtained. The suspension of nanoparticles is finally freeze-dried.

The contents of leucine motifs are determined by proton nuclear magnetic resonance (signals at 2.10, 2.22 and 2.58 ppm for 4H of Glu and at 0.85 ppm for 6H of Leu). The mean hydrodynamic diameter Dh is measured according to Md on aqueous suspensions of the freeze-dried products. The insulin load factor is determined according to Ma.

Example 6

Production, in stable aqueous colloidal suspension of vector nanoparticles, from a block polyamino acid, poly(Leu/Glu) 50/150 diblock and characteristics of the nanophases 46.4 g of NCA-GluOMe (0.248 mol) and 186 g of N-methyl-2-pyrrolidinone (NMP) are introduced, with stirring, into a 0.5 liter reactor thermostate at 30° C. After dissolution, 6.90 g of a 0.19 M solution of ammonia in methanol (1.25 mol %/NCA) are added. The polymerization is monitored by measuring the carbon dioxide emitted into a gas bell jar and verified by disappearance of vibration bands characteristic of the NCAs at 1860 and 1790 $cm^{-1}$. After 30 min, a solution of 12.97 g of NCA Leucine (0.083 mol) in 218 g of NMP is introduced. After 10 min of reaction, the temperature is increased to 60° C. The polymerization is monitored as above and is complete after 1–2 hours. The temperature of the reaction mixture obtained previously is increased to 80° C. 40.3 g of aqueous hydrochloric acid (35% of the mass) are added, with mechanical stirring over 30 min, to the reaction mixture. The reactor is then placed under reduced pressure regulated at 600 mBar for 6 hours. A mixture of 40.3 g of 35% hydrochloric acid and of 161.3 g of water is then added over 60 min, followed by a second phase of vacuum at 250 mBar for 18 hours. The reaction mixture is then cooled to 50° C. and then neutralized with aqueous sodium hydroxide (35% by mass).

The NMP and the sodium chloride formed during the neutralization are removed by diafiltration against 20 volumes of Milli Q water, on a membrane with an NWCO of 1 000 Daltons (Pellicon II system, Millipore). A stable aqueous colloidal suspension of vecotr nanoparticles is thus obtained. The suspension of nanophases is finally freeze-dried.

The contents of leucine motifs are determined by proton nuclear magnetic resonance (signals at 2.10, 2.22 and 2.58 ppm for 4H of Glu and at 0.85 ppm for 6H of Leu). The mean hydrodynamic diameter Dh is measured according to Md. The insulin load factor is determined according to Ma.

Example 7

Comparative example of the nature of the particles formed with the teaching of PCT patent WO 96/29991

The particles obtained by the teaching of patent WO 96/2991 are those which appear in FIG. 1. Advantageously, the particles according to the invention are those which appear in the appended FIG. 2 corresponding to a photograph taken under a transmission electron microscope.

Figure 2:
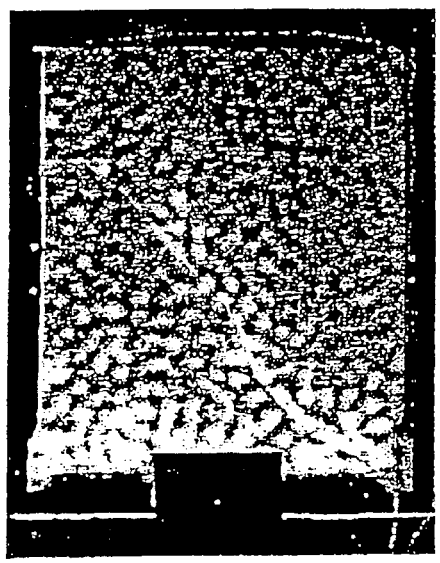
FIG. 2: Nanoparticles obtained with the block copolymer according to the present invention (example 2). It will be noted that the bar now represents here only 50 nm.

The differences in morphology and size appear blatantly on comparing FIG. 1 which represents PVs according to the prior art, on the one hand, and FIG. 2 showing PVs according to the invention, on the other hand. A notable difference in morphology is observed here. The PVs of FIG. 2 are such that the majority of the larger-sized particles exhibit an oblong shape.

Example 8

Test of stability of a colloidal suspension prepared according to Example 2 with the polymer poly(Leu/Glu) 40/80

The pulverulent powder of Example 2 is dissolved in an amount of 60 mg/ml of powder in a phosphate buffer. The pH was adjusted to 7.3 and the osmolality of the suspension was adjusted to 300 mOsm/kg using a 5 M NaCl solution. The solution was filtered (0.22 μm) before being distributed at the rate of 5 ml into sterile 10 ml bottles. The stability of the samples was evaluated over a period of 4 months. Half of the samples were kept at 4° C. (±2° C.) while the other samples were maintained at laboratory temperature:25° C. (±5° C.). At given times, the samples are collected from the site of storage and equilibrated for 1 hours at room temperature before the analysis. The analytical methods are detailed, the results being presented in the form of two tables.

1) Verification of the homogeneity of the colloidal solution: Without stirring the suspension, 100 μl samples are collected thee times in order to represent the state of the solution at the top, in the middle and at the bottom of the bottle. The refractive index of each sample is measured at 25° C. on an Abbe refractometer calibrated relative to pure water. Three readings are made for each sample and the three mean values are compared. Any variation in the concentration of the solution results in a difference in refractive index.

2) Measurement of the hydrodynamic diameter: A 100 μl sample of the solution to be analyzed is diluted 120-fold with a 0.15 M NaCl solution and the Dh of the colloidal particles is measured according to the protocol Md.

3) Measurement of the viscosity: The measurements are carried out on 0.75 ml samples using an AR1000 rheometer (TA instruments) equipped with a Cone/Plane geometry (cone 4 cm/2° C.) at a temperature of 20.0° C. +/− 0.1° C. (regulation by Pelletier effect). The viscosity curve as a function of the shear gradient is recorded for gradients varying from 1 to 100 $s^1$. At these concentrations, the solutions are slightly rheofluidizing and the viscosity value selected is taken for a gradient of 10 $s^{-1}$.

The results obtained after aging at 4° C. and 25° C. are assembled in Tables I and II.

TABLE I

Aging at 4° C.

|  |  | To | T1 | T2 | T3 | T4 | T5 |
|---|---|---|---|---|---|---|---|
| number of days of aging |  | 0 | 9 | 28 | 59 | 92 | 127 |
| homo- | sample 1 cm | 1.3443 | 1.3442 | 1.3447 | 1.3438 | 1.3440 | 1.3443 |
| geneity | sample 1.5 cm | 1.3442 | 1.3442 | 1.3446 | 1.3439 | 1.3439 | 1.3440 |
| (index) | sample 2 cm | 1.3443 | 1.3442 | 1.3448 | 1.3439 | 1.3440 | 1.3440 |
| hydrodynamic diameter (nm) |  | 45 | 45 | 44 | 43 | 44 | 44 |
| Viscosity (mPa.s) |  | 246 | 246 | 250 | 250 | 262 | 250 |

TABLE II

Aging at 25° C.

|  |  | To | T1 | T2 | T3 | T4 | T5 |
|---|---|---|---|---|---|---|---|
| number of days of aging |  | 0 | 9 | 28 | 59 | 92 | 127 |
| homo- | sample 1 cm | 1.3443 | — | 1.3448 | 1.3441 | 1.3440 | 1.3442 |
| geneity | sample 1.5 cm | 1.3442 | — | 1.3448 | 1.3441 | 1.3440 | 1.3442 |
| (index) | sample 2 cm | 1.3443 | — | 1.3447 | 1.3441 | 1.3440 | 1.3442 |
| hydrodynamic diameter (nm) |  | 45 | — | 44 | 44 | 45 | 46 |
| viscosity (mPa.s) |  | 246 | — | 246 | 250 | 284 | 240 |

Example 9

Figure 3:
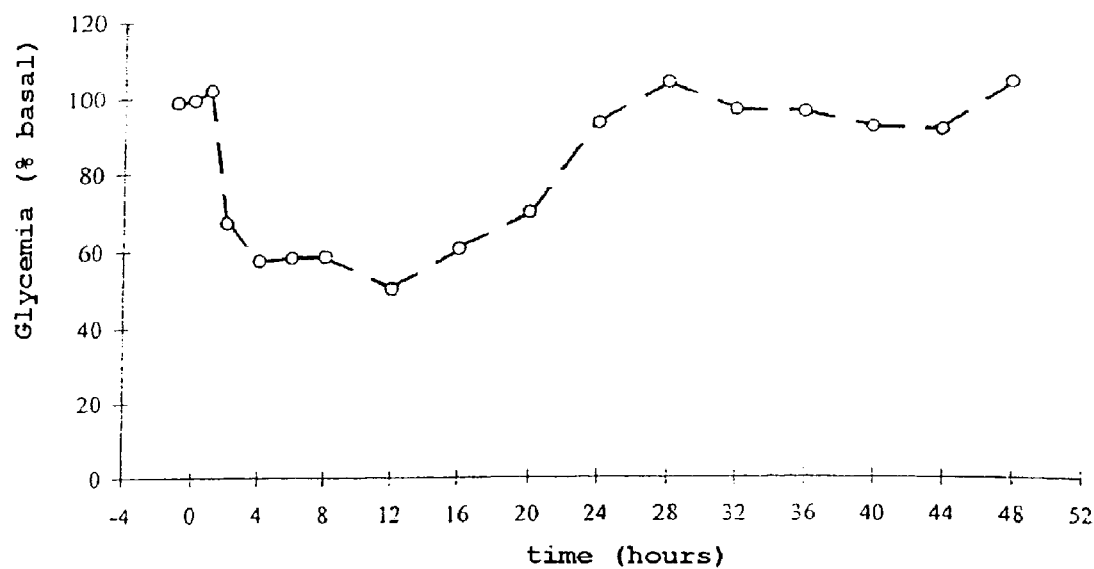
FIG. 3: Variation in the glucose concentration (mean at % basal on 4 dogs) after injection of a PV formulation loaded with insulin in an amount of 2 IU/kg.
Figure 4:
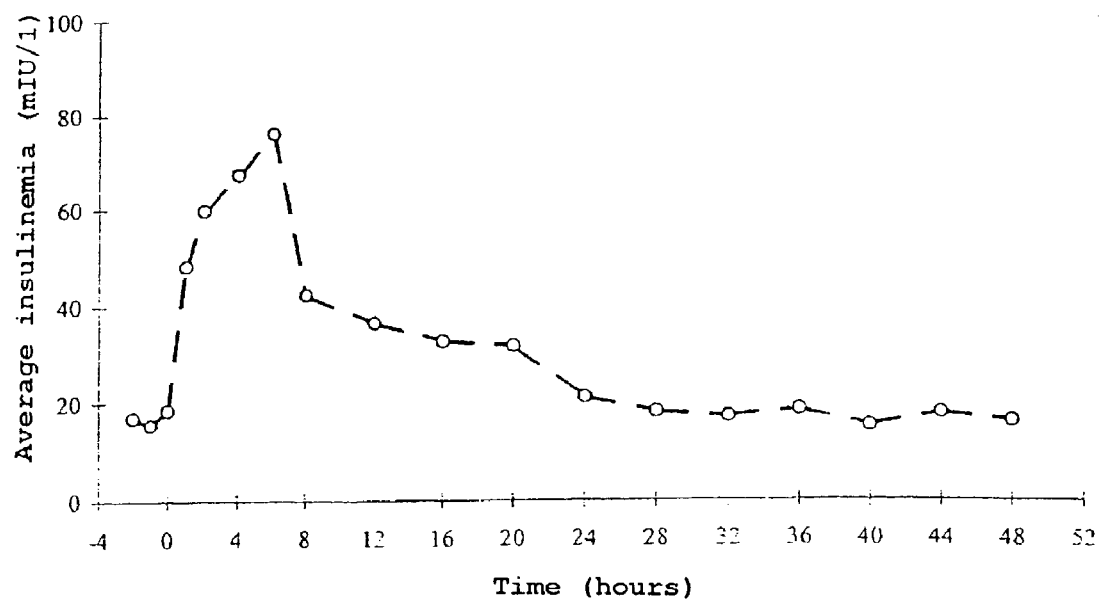
FIG. 4: Variation in the serum insulin concentration (mean on 4 dogs) after injection of a PV formulation loaded with insulin in an amount of 2 IU/kg.

Test of release of insulin in animals after administration of a suspension of particles containing insulin A formulation is prepared from PV (of Example 3) and insulin, the quantity of each being determined according to measurements of combination rate (Ma). A group of 4 beagle dogs (males and females) weighing between 10 and 12 kg are fasted for 18 hours. A preparation is formulated and is composed of 80 IU of insulin t 56 mg of PV in 1 ml of PBS buffer. The dogs then receive a subcutaneous administration of this insulin preparation at the rate of 2 IU/kg of weight. Blood sample collected for glucose and insulin assay before (−2h, −1h and 0h) and after (1h, 2h, 4h, 6h, 12h, 16h, 20h, 24h, 28h, 32h, 36h, 40h, 44h, 48h) the injection. The glucose concentrations are measured in the samples by the glucose oxidase method and serum insulin is assayed using a radioimmunological method. FIG. 3 gives the mean of the variation in glucose for this formulation. FIG. 4 gives the mean of the variation in serum insulin for this formulation.

This example shows, through the biological activity, the nondenaturation of the protein as well as the possibility of prolonging the release by >24h, two advantageous aspects of the present invention.

The invention claimed is:

1. A stable colloidal suspension comprising submicronic particles, wherein the particles:

are individualized supramolecular arrangements;

are in a nondissolved state;

spontaneously associate with at least one active principle if at least one active principle is added to the colloidal suspension;

if loaded with at least one active principle, release the at least one active principle in either or both a prolonged manner or a delayed manner;

are stable at a pH of between 4 and 13 in the absence of a surfactant;

comprise linear peptide linked amphiphilic polyamino acids (PAA) comprising recurring hydrophilic amino acids (AAI) with ionizable side chains and recurring hydrophobic neutral amino acids (AAO);

have a load factor (Ta) with insulin, expressed as % by weight of combined insulin relative to the mass of PAA particles, that is $\geq 7\%$ and <25%; and have a mean hydrodynamic diameter (Dh), expressed in nm, that is 10 nm$\leq$Dh$\leq$150 nm.

2. The colloidal suspension of claim 1, wherein:

the recurring hydrophilic amino acids are glutamate, aspartate, glutamic acids, aspartic acids, or mixtures thereof, the recurring hydrophobic neutral amino acids are leucines, isoleucines, valines, alanines, glycines, phenylalanines, or mixtures thereof, the load factor is 8%$\leq$25%, and the mean hydrodynamic diameter is 20 nm$\leq$Dh$\leq$100 nm.

3. The colloidal suspension of claim 2, wherein the recurring hydrophilic amino acids are glutamic acids, and the recurring hydrophobic neutral amino acids are leucines, and the load factor is 10%≦Ta≦25%.

4. The colloidal suspension of claim 1, wherein the constituent PAA of the particles are block PAA in which:
the molar ration is 10%≦AAO/(AAI+AAO)≦70%, and the degree of polymerization of the chain is between 30 and 600.

5. The colloidal suspension of claim 1, wherein the constituent PAA of the particles are diblock PAA.

6. The colloidal suspension of claim 1, wherein the suspension is aqueous and stable.

7. The colloidal suspension of claim 1, wherein the amphiphilic polyamino acids of the particles comprise α-peptide linkages.

8. The colloidal suspension of claim 1, wherein the suspension further comprises at least one principle loaded onto the particles.

9. The colloidal suspension of claim 8, wherein the at least one active principle is a hemoglobin, a cytochrome, an albumin, an interferon, an antigen, an antibody, erythropoietin, insulin, a growth hormone, factor VIII, factor IX, an interleukin, a hematopoiesis-stimulating factor, heparin, an RNA, a DNA, an anthracycline, a taxoid, or a mixture thereof.

10. The colloidal suspension of claim 8, wherein the at least one active principle further comprises a nutritional, plant-protective, or cosmetic active principle.

11. A method for preparing the colloidal suspension of claim 1, comprising
 a. copolymerizing N-carboxy anhydride (NCA) forms of i) monomers of precursors of hydrophilic amino acids with ionizable side chains and ii) monomers of hydrophobic neutral amino acids in the presence of at least one non-aromatic polar solvent selected from the group consisting of N-methylpyrrolidone (NMP)), dimethylformamide (DMF), dimethyl sulfoxide (DMSO), dimethylacetamide (DMAc) and pyrrolidone, and optionally in the presence of at least one cosolvent selected from the group consisting of aprotic solvents, protic solvents, water, and alcohols;
 b. converting the hydrophilic amino acid precursors in the copolymer formed in (a) to hydrophilic amino acids by adding an aqueous acid to the medium of (a);
 c. neutralizing the reaction medium of (b); and
 d. removing the solvents and the salt formed after the neutralization step to thereby produce a purified colloidal suspension of particles comprising the copolymer in aqueous media.

12. The method of claim 11, wherein the hydrophilic amino acids are glutamic acids, aspartic acids, or mixtures thereof, and the hydrophobic neutral amino acids are leucines, isoleucines, valines, alanines, glycines, phenylalanines, or mixtures thereof.

13. The method of claim 11, wherein the hydrophilic amino acids are glutamic acids and the hydrophobic neutral amino acids are leucines.

14. A method for preparing a pulverulent solid comprising submicronic particles, comprising:
 a) optionally concentrating the colloidal suspension obtained in step (c) or step (d) of claim 11; and
 b) removing the liquid medium to thereby collect a pulverulent solid comprising submicronic particles.

15. A pulverulent solid comprising submicronic particles produced by the method of claim 14.

16. A pharmaceutical, nutritional, plant-protective, or cosmetic product comprising the pulverulent solid produced by the method of claim 14.

17. A method for preparing the colloidal suspension of claim 8, comprising contacting the colloidal suspension of claim 8 with a liquid phase containing the at least one active principle, to thereby obtain a colloidal suspension of particles loaded with at least one active principle.

18. A method of preparing the colloidal suspension of claim 8, comprising contacting the colloidal suspension of claim 1 with a solid phase containing the at least one active principle, to thereby obtain a colloidal suspension of particles loaded with at least one active principle.

19. A pulverulent solid comprising submicronic particles, wherein the pulverulent solid is produced by removing liquid from the colloidal suspension of claim 1, to thereby produce a pulverulent solid comprising submicronic particles.

20. A method for preparing a colloidal suspension of submicronic particles, comprising contacting the pulverulent solid of claim 19 with a nonsolvent aqueous medium.

21. A method for preparing a colloidal suspension of submicronic particles loaded with at least one active principle, comprising contacting the pulverulent solid of claim 19 with a liquid phase containing the at least one active principle to thereby produce a colloidal suspension of submicron particles loaded with at least on active principle.

22. A method for preparing a colloidal suspension of submicronic particles loaded with at least one active principle, comprising contacting the pulverulent solid of claim 19 with at least one active principle in solid form to form a mixture, and then dispersing the mixture of solids in an aqueous solution to thereby produce a colloidal suspension of submicron particles loaded with at least one active principle.

* * * * *